United States Patent [19]
Bales et al.

[11] Patent Number: 5,171,258
[45] Date of Patent: Dec. 15, 1992

[54] DOUBLE ACTING, DUAL PIVOT DISPOSABLE LAPAROSCOPIC SURGICAL INSTRUMENTS

[75] Inventors: Thomas O. Bales, Coral Gables; Jurgen Kortenbach, Ft. Lauderdale, both of Fla.

[73] Assignee: Symbiosis Corporation, Miami, Fla.

[21] Appl. No.: 780,014

[22] Filed: Oct. 21, 1991

Related U.S. Application Data

[63] Continuation-in-part of Ser. No. 521,766, May 10, 1990, and a continuation-in-part of Ser. No. 680,395, Apr. 4, 1991.

[51] Int. Cl.⁵ .............................................. A61B 17/00
[52] U.S. Cl. .................................... 606/205; 606/174; 606/170; 128/751
[58] Field of Search ................. 30/155, 242, 250, 251, 30/266, 267, 335; 285/921; 128/749, 751; 606/205, 206, 207, 208, 167, 170, 174; 74/105

[56] References Cited

U.S. PATENT DOCUMENTS

| | | |
|---|---|---|
| 3,895,636 | 7/1975 | Schmidt ............................... 606/205 |
| 4,664,471 | 6/1987 | Hayashi ............................... 606/205 |
| 4,896,678 | 1/1990 | Ogawa ................................. 128/751 |
| 4,982,727 | 1/1991 | Sato ..................................... 606/205 |

*Primary Examiner*—Francis Jaworski
*Assistant Examiner*—Scott R. Akers
*Attorney, Agent, or Firm*—David P. Gordon

[57] ABSTRACT

Disposable laparoscopic surgical instruments for insertion through trocar tubes are disclosed. The instruments broadly include: a hollow aluminum tube; an aluminum clevis which is formed separately from the aluminum tube with the distal end of the hollow aluminum tube crimped around the proximal end of the clevis, and with the clevis including an axially off-set pivot pin; at least one end effector element having a pivot hole through which the off-set pivot pin of the clevis is pivotally engaged, and another through-hole; an aluminum push rod extending at least partially through the hollow aluminum tube and mechanically coupled to the end effector element; and apparatus for imparting reciprocal motion to the push rod relative to the aluminum tube, whereby the reciprocal motion is translated at an offset pivot of the clevis into a high torque pivotal motion of the end effector element.

20 Claims, 8 Drawing Sheets

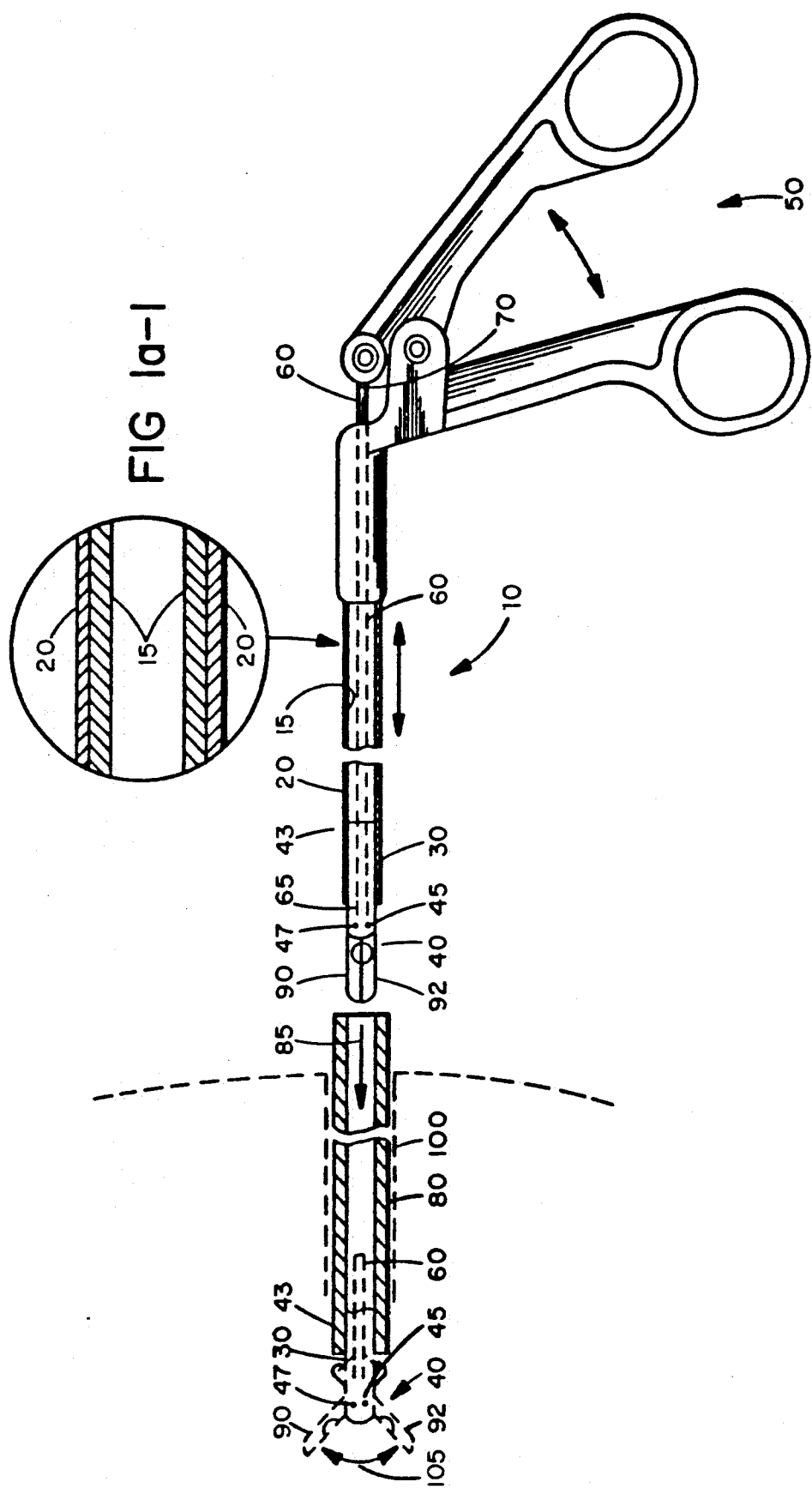

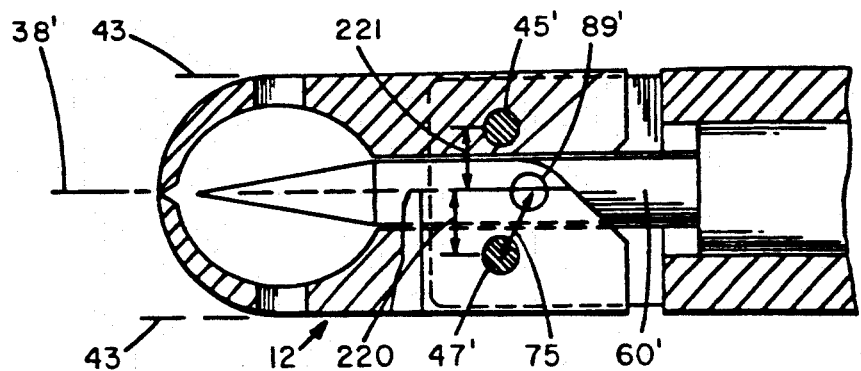
FIG. 4
PRIOR ART
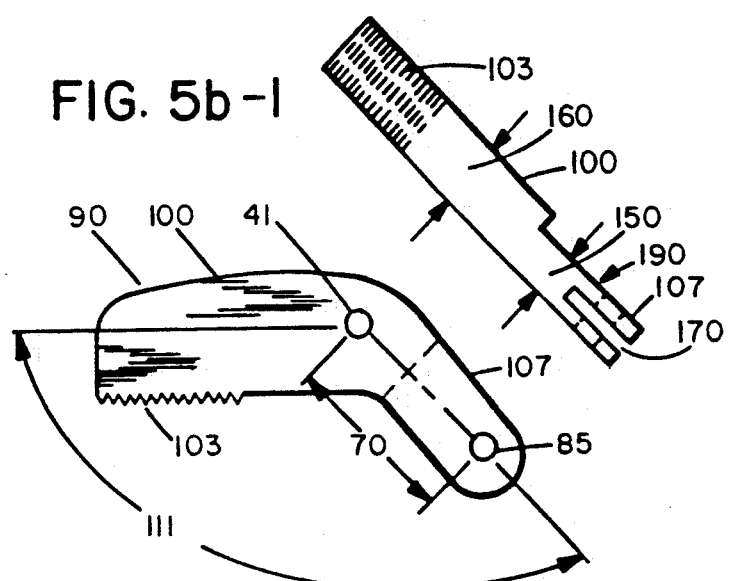
FIG. 5b-1
FIG. 5b
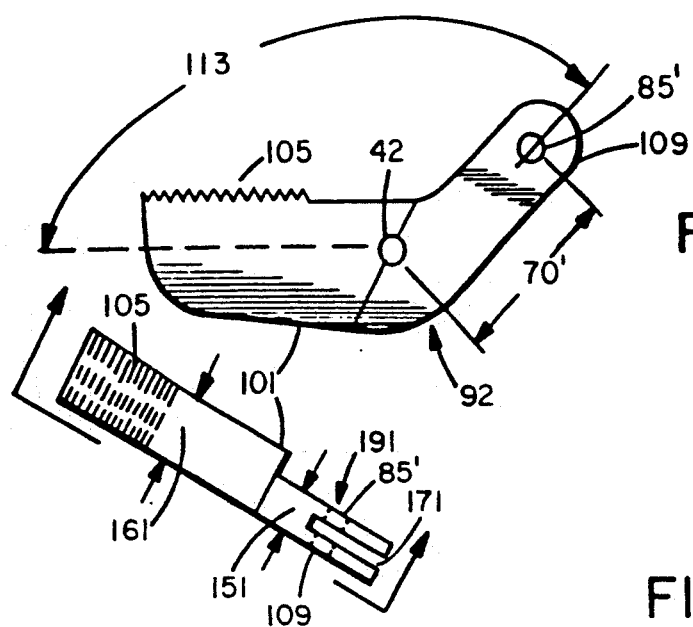
FIG. 5a
FIG. 5a-1

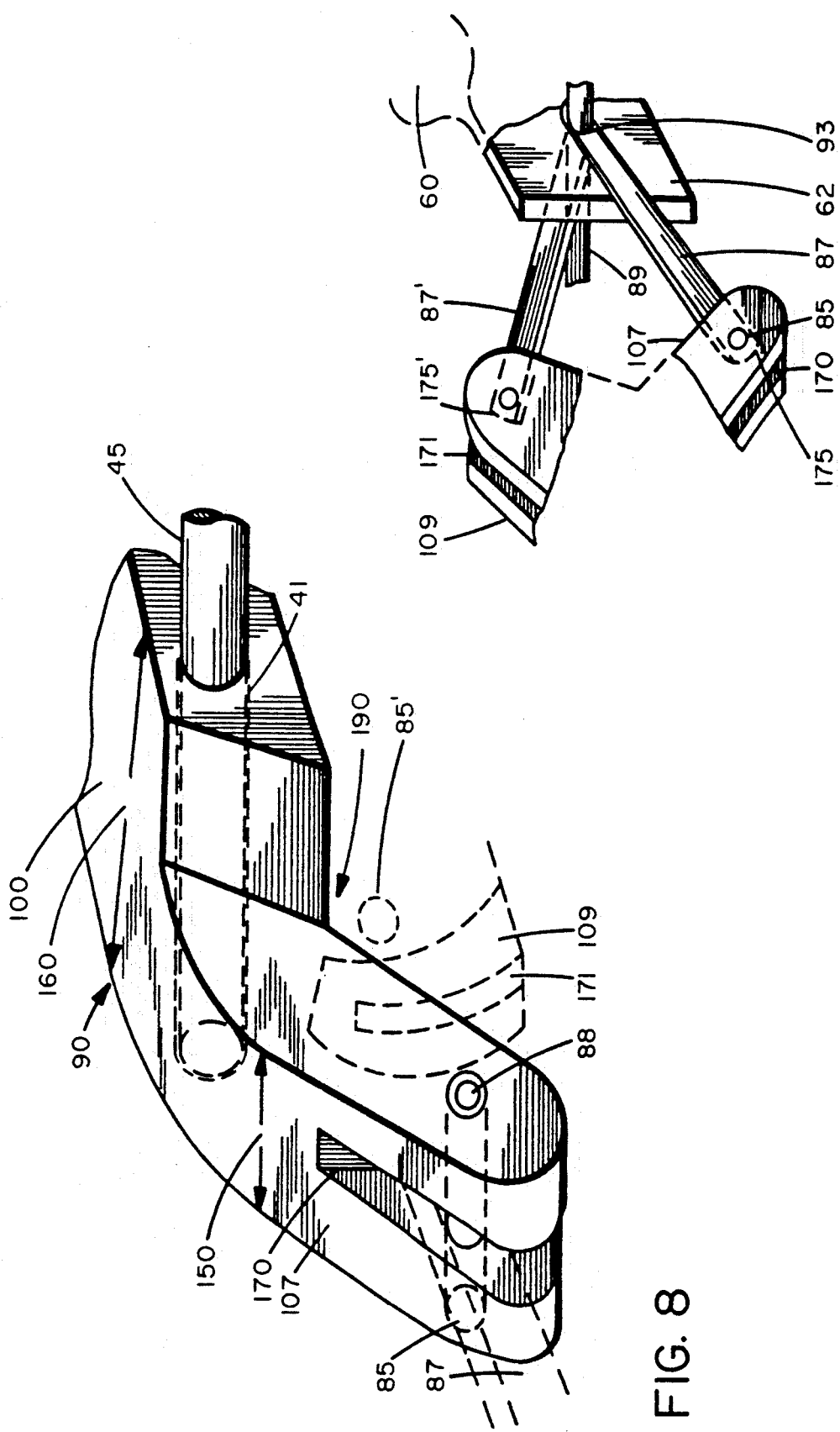

DOUBLE ACTING, DUAL PIVOT DISPOSABLE LAPAROSCOPIC SURGICAL INSTRUMENTS

This is a continuation-in-part of U.S. Ser. No. 07/521,766 filed May 10, 1990 and U.S. Ser. No. 07/680,392 filed Apr. 4, 1991 which are hereby incorporated by reference herein in their entirety.

BACKGROUND OF THE INVENTION

The present invention broadly relates to laparoscopic surgical instruments. More particularly, the invention relates to disposable surgical instruments which include disposable end effectors such as cutters, graspers, and dissectors which are useful in a laparoscopy procedure.

The laparoscopy procedure has recently become a widely practiced surgical procedure. A laparoscopy procedure typically involves incising through the navel and through the abdominal wall for viewing and/or operating on the ovaries, uterus, gall bladder, bowels, appendix, although more recently, incisions and insertion of trocar tubes have been made in different areas of the abdomen and even in the chest cavity. Typically, trocars are utilized for creating the incisions. Trocar tubes are left in place in the abdominal wall so that laparoscopic surgical tools may be inserted through the tube. A camera or magnifying lens is often inserted through the largest diameter trocar tube (e.g. 10 mm diameter) which is generally located at the navel incision, while a cutter, dissector, or other surgical instrument is inserted through a similarly sized or smaller diameter trocar tube (e.g. 5 mm diameter) for purposes of manipulating and/or cutting the internal organ. Sometimes it is desirable to have several trocar tubes in place at once in order to receive several surgical instruments. In this manner, organ or tissue may be grasped with one surgical instrument, and simultaneously may be cut or stitched with another surgical instrument; all under view of the surgeon via the camera in place in the navel trocar tube.

Previous to the present invention, laparoscopic tools have utilized connecting mechanisms for imparting pivotal motion to the manipulating members of the end effectors. These tools, however, have utilized either single pivot mechanisms specifically designed to avoid protrusions outside of the outline of the laparoscopic tool so as to avoid any inadvertent contact with tissue of a patient, or double pivot mechanisms such as disclosed in U.S. Pat. No. 3,895,636 to Schmidt where the manipulating members are directly actuated by the axial movement of a common reciprocating member. While such tools have functioned adequately for many of their intended purposes, these laparoscopic tools have not enabled the desired amount of gripping or cutting force important in the manipulation of large vessels or organs, such as might be required in procedures involving, e.g., intestinal organs.

SUMMARY OF THE INVENTION

It is therefore an object of the invention to provide disposable laparoscopic surgical instruments particularly suited for surgical procedures involving larger organs, such as intestinal organs.

Another object of the invention is to provide disposable laparoscopic surgical instruments of improved design with high leverage end effectors and with connecting mechanisms of very small cross section which do not protrude outside of the envelope of the instrument.

It is a further object of the invention to provide a disposable laparoscopic surgical instrument which utilizes an improved linkage system which enables increased leverage to be applied to the manipulation members of the end effector of the instrument.

In accord with the objects of the invention, a disposable laparoscopic surgery instrument generally includes: a tube; a push rod which extends through the tube; an actuating means engaging the tube and the push rod for imparting reciprocal axial motion to the push rod; end effector means coupled at their proximal ends to the push rod by connecting means which are also coupled to the push rod; a clevis coupled to the tube at its proximal end and to the end effector means at its distal end; and posts coupled to the clevis and extending through the end effector means such that the end effector means rotate thereabout, with the posts being transverse and displaced relative to the longitudinal axis of the tube, wherein axial movement of the push rod effects movement of the end effector means in a plane parallel to the longitudinal axis of the push rod.

Plastic shrink wrap is preferably utilized to electrically insulate the disposable instrument and extends over the aluminum tube and over at least an adjacent portion of the clevis. The tube and push rod are preferably made of aluminum, the clevis is preferably made of a high-strength aluminum alloy, the actuating means is preferably made of plastic and aluminum, and the end effector means is preferably made of investment cast bronze.

The clevis of the invention is preferably a separately formed clevis having a knurled rod-like proximal end for mating with the end of the aluminum tube, and a U-shaped distal portion for supporting the posts which around which the end effector means rotate. A first post in the distal portion of the clevis is perpendicular to the legs of the U-shaped distal portion and transverse to the longitudinal axis of the aluminum tube and the push rod. The post is displaced from the longitudinal axis and arranged to extend through hole(s) in the manipulating members of the end effector means. The second transverse post is provided adjacent to and opposite the first post on the opposite side of the longitudinal axis. In this manner, the blades or prongs of the manipulating members of the end effector means are held by respective axially offset pivot posts and can respectively rotate around the posts. A high degree of leverage is thereby developed in the manipulation members of the end effector.

The end effector means of the invention can take any of many forms, such as, e.g., a scissors, a dissector, or a grasper. Additionally, the end effector means can be double acting (i.e., both end effectors moving) or single acting (i.e., one moving end effector and one fixed end effector which is does not have a connecting means but which is fixed to the clevis by use of a boss extending from the end effector into a hole in a clevis leg). Regardless of the type of end effector utilized, each manipulation member of the end effector is arranged with a hole to accept a post of the clevis so that each manipulation member rotates around a different post.

According to one aspect of the invention, the push rod is flattened on its distal end, and the linkage means which couple the push rod and the end effectors both extend through a hole in the flattened end of the push rod as well as through other holes in the proximal ends of the end effectors. Because the outer tube is positioned at a fixed distance from the rotation hole in the end effector (due to the clevis), when the push rod is moved axially relative to the tube, the end effectors cannot move axially. However, because the push rod is also a fixed distance away from holes in the proximal ends of the end effectors (due to the connecting means), movement of the push rod relative to the tube causes rotation of the end effectors in a plane. In other words, movement of the push rod relative to the tube causes the holes through the end effectors through which the linkage members extend to rotate along arcs centered at the rotation holes in the end effectors through which the transverse posts extend. Movement in this manner typically effects a cutting, dissecting or grasping action.

Single acting end effectors can include one hole in the flattened end of the push rod and one linkage member for connecting the moving prong or blade to the push rod. If desired, single acting end effectors can be implemented by forming one end of a pull wire into a "dog's leg" and by inserting the dog's leg pull rod end into the hole in the proximal end of the end effector. Regardless, of the arrangement provided for the moving end effector, in accord with the invention, the fixed end effector is provided as a separate piece and is fixed into the clevis by use of a boss extending from the fixed end effector.

A better understanding of the disposable laparoscopic surgical instruments of the invention, and additional advantages and objects of the invention will become apparent to those skilled in the art upon reference to the detailed description and accompanying drawings.

BRIEF DESCRIPTION OF THE DRAWINGS

FIG. 1 is a side elevation view, partly in section, of a disposable laparoscopic instrument prior to insertion into a trocar tube, and, in partial phantom format, after insertion into a trocar tube;

FIG. 1a-1 is a cross section through FIG. 1 at the indicated location thereof;

FIG. 2b is a cross-section view of the device of FIG. 2a;

FIG. 3a is a partially broken-away side elevation view of the actuating handle of the disposable laparoscopic instrument of the invention;

FIG. 3b is a rear elevation view of the device of FIG. 3a;

FIG. 4 is a side elevation view of a prior art instrument;

FIGS. 5a and 5b are side views, and FIGS. 5a-1 and 5b-1 are top views of the elements of the device of FIG. 5;

FIG. 8 is a partial perspective view of a manipulation member of an end effector; and FIG. 9 is a partial perspective view of the linkage shown in FIG. 5.

DETAILED DESCRIPTION OF THE PREFERRED EMBODIMENT

Figure 2B:
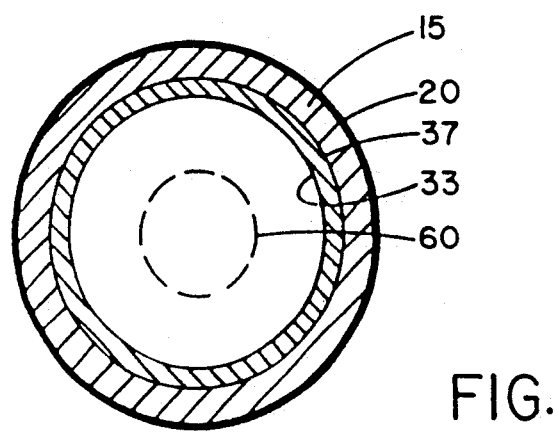

With reference to FIGS. 1 and 1a-1, a disposable laparoscopic surgical instrument is indicated at 10. The disposable laparoscopic surgical instrument 10 includes an aluminum tube 15 surrounded by a peripheral insulating shrink wrap layer of plastic 20, a clevis means 30, end effectors 40, actuating means 50, and a push rod 60. The clevis means 30 is advantageously a separately formed aluminum piece which fixedly engages aluminum tube 15 as described in more detail hereinafter. The clevis 30 also engages the manipulating members 90, 92 of the end effector 40 which are respectively pivotally engaged to clevis 30 at pivot pins 45, 47 as hereinafter more particularly described. End effector 40 is preferably formed of investment cast bronze as disclosed in copending U.S. Ser. No. 07/521,766 which was previously incorporated by reference herein, or can be formed of investment cast stainless steel, other metals, or plastic as desired. The push rod 60, which is also preferably formed of stainless steel, is engaged at its distal end 65 to the end effector 40, as hereinafter more fully described, and is connected at 70, at its proximal end, to a manually operable actuating means 50. For purposes herein, the "distal end" of the instrument 10 or any part thereof, is the end closest to the surgical site and distant from the surgeon, while the "proximal end" of the instrument 10 or any part thereof, is the end most proximate the surgeon and distant the surgical site.

In use, the laparoscopy instrument 10 is inserted with the manipulation members, e.g. blades or graspers 90, 92 of the end effector 40, in the closed position, into trocar tube 80, as indicated at the arrow 85 of FIG. 1. The distal portion of the instrument 10 passes through the trocar tube 80 into body incision 100. Upon the distal portion of the laparoscopy instrument 10 exiting the trocar tube 80, the manipulating members, e.g. blades 90, 92 can be opened and closed as indicated at 105 by reciprocal motion of push rod 60 which results from operation of the manual actuating means 50. As is discussed more fully hereinafter, the clevis effectively translates the reciprocal motion of the push rod 60 into the end effector means action indicated at 105.

Figure 2A:
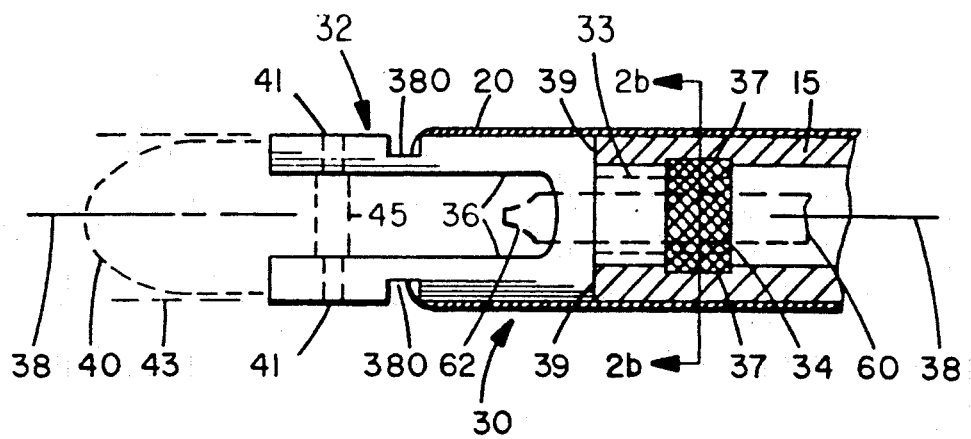
FIG. 2a is a side elevation view, partly in section, of the clevis of the invention in conjunction with the distal end of the tube and shrink wrap of the invention.
Figure 2C:
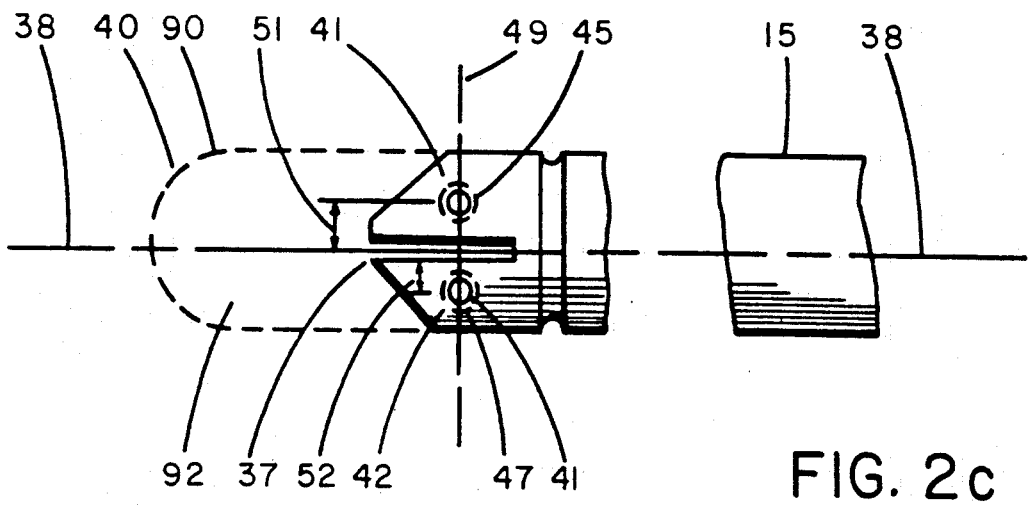
FIG. 2c shows the device of FIG. 2a rotated by 90°.
Figure 2D:
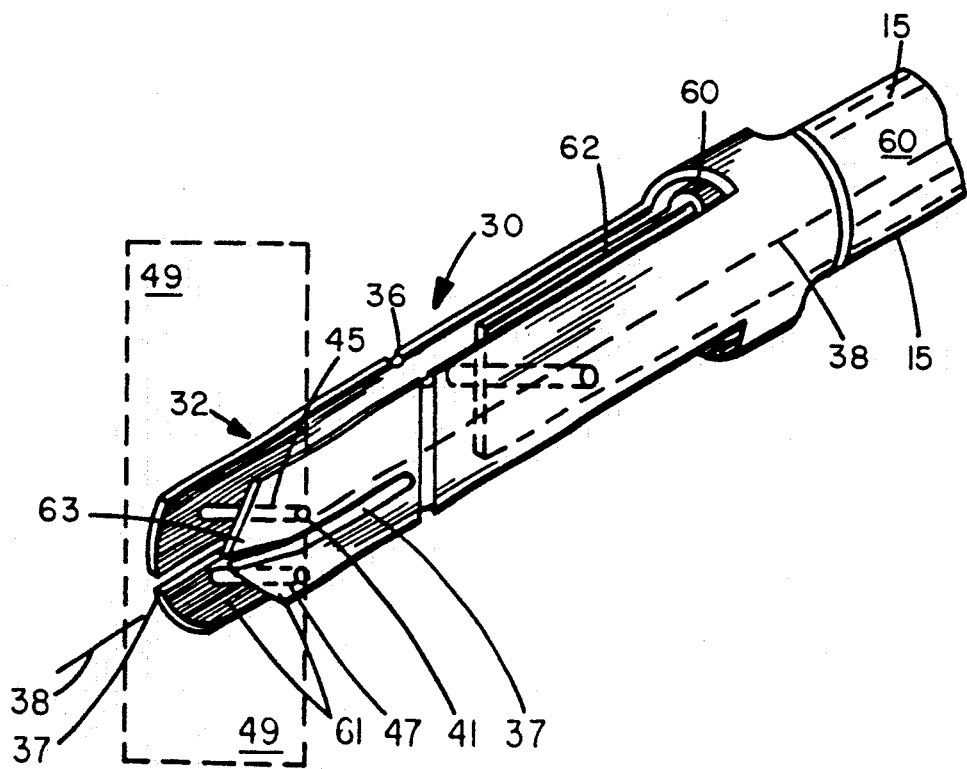
FIG. 2d is a perspective view of the clevis element shown in FIG. 2a, along with the transverse posts.

Turning to FIGS. 2a, 2b, 2c and the perspective view of FIG. 2d, a preferred configuration of the clevis 30 of the present invention is seen. The clevis has a knurled rod-like proximal portion 34 for mating with the end of the aluminum tube 15, and a post-supporting U-shaped distal portion 32 for holding the end effector means. The proximal portion 34 of the clevis is preferably hollow, as indicated at 33, to permit the push rod 60, with its flattened terminal portion 62 to extend therethrough. The distal portion 32 of the clevis 30 is provided with a first post or pivot pin 45, a second post or pivot pin 47, and legs 36, which have slots 37 to increase their flexibility and to allow independent adjustement of the two pivot posts 45 and 47. The posts 45, 47 are generally perpendicular, i.e. transverse, to the legs 36 of the clevis and are arranged to extend respectively through holes 41, 42 in the manipulation members 90, 92 of end effector means 40. In this manner, the blades or prongs 90, 92 of the end effector means 40 are held by, but can rotate around the posts 45, 47 (i.e. they are rotatably respectively engaged therewith) which are symmetrically disposed about longitudinal axis 38 and which are in a common plane which is transverse to longitudinal axis 38. Push rod 60, tube 15 and clevis 30 all have substantially the same common longitudinal axis 38. Posts 45, 47 are transverse to and displaced from axis 38 on opposite sides thereof as indicated at 51, 52 in FIG. 2c.

As seen in FIG. 2a, a recess or notch 380 is provided which extends across each leg 36 of the clevis 30. Consequently, a peripherally applied electrically insulating plastic wrap 20 can be end-cut at recess 380 and a smooth transition from the end effector means 40 via the clevis 30 to tube 15 can be achieved. Even if slight outward flaring of wrap 20 occurs at the end-cut, as is common, this flaring can be tolerated as it will be within the envelope of the normal outer instrument surface indicated at 43.

Clevis 30 is preferably made from a high strength aluminum base alloy (e.g. 2024 alloy of Alcoa) which is preferably harder than the aluminum base alloy (e.g. 6061 or 6063 alloys of Alcoa) from which tube 15 is fabricated. The post elements 45, 47 portion of the clevis 30 may be made out of a high strength aluminum alloy or, for added strength, out of a stainless steel screw or nail. In assembly of the laparoscopy surgical instrument 10, serrated or knurled portion 34 of clevis 10 is fit snugly into tube 15 such that the walls of tube 15 abut the peripheral shoulder 39 of clevis 30, with the outer surface of tube 15 and the adjacent outer surface of clevis 30 having essentially the same diameter. Mechanical pressure is then applied to tube 15 peripherally at the location of knurled portion 34, thereby crimping the end portion of tube 15 onto the knurled portion 34. Mechanical pressure causes the projections of the knurls to bite into and firmly engage tube 15 as indicated at 37 due to the higher hardness of the clevis material. Alternately, the clevis may be pressed into the tube. Once the clevis 30 and tube 15 have been properly joined, the plastic shrink wrap 20 can be applied over the tube 15 and an adjacent portion of the clevis 30 and end-cut at recess 380. Alternately, the plastic shrink wrap may be applied after the end effectors are attached to the instrument by the posts as hereinafter described.

Figures 3A, 3B:
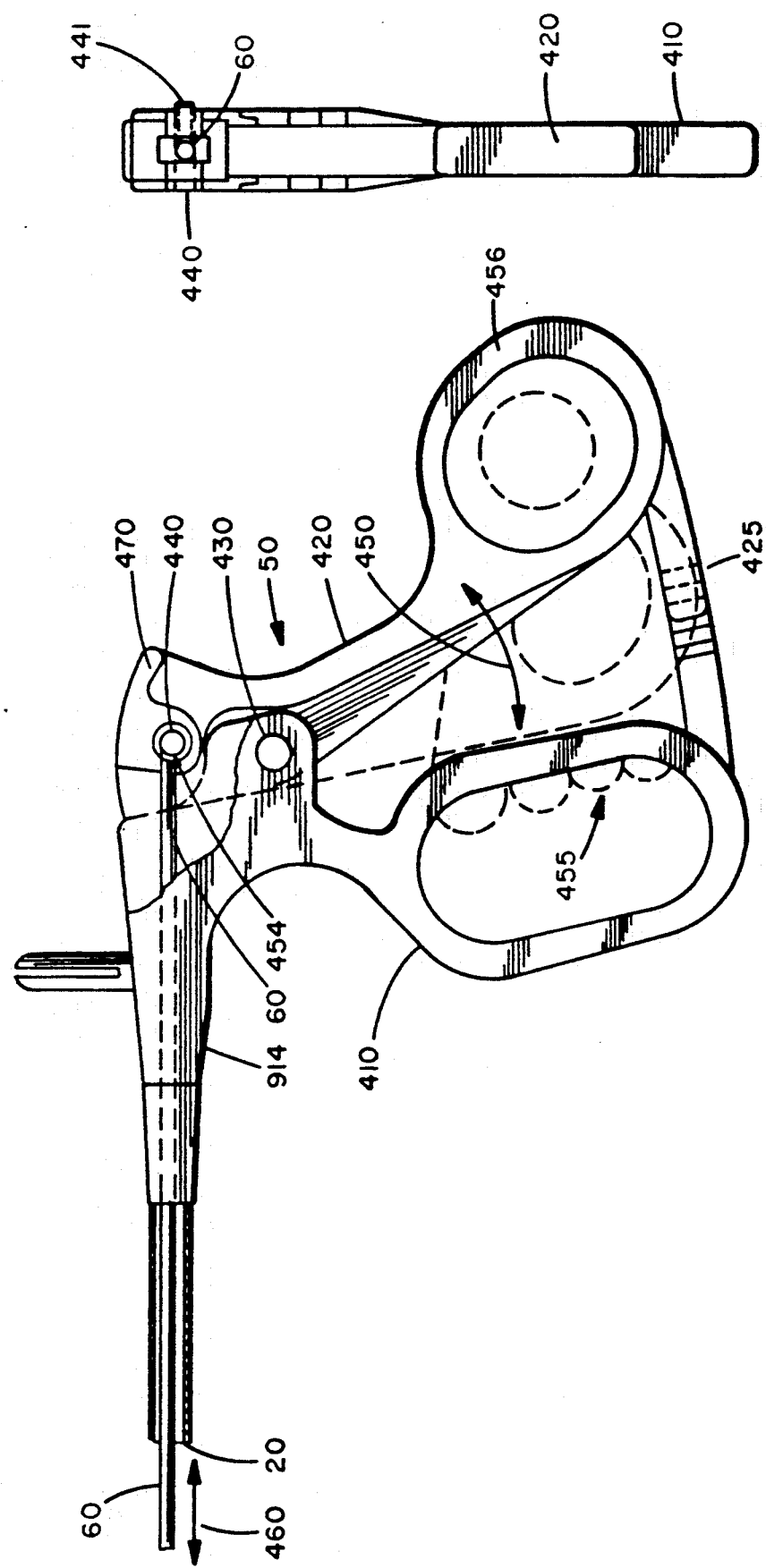

With reference to FIGS. 3a and 3b, manually operable actuating means are indicated at 50 which includes an electrically insulating housing 914 having a fixed handle portion 410 integral therewith and a lever portion 420 pivotally engaged to housing 914 at pivot pin 430. Push rod 60 passes through aluminum tube 15 (covered by shrink wrap 20) and engages cross pin 440 at 454; set screw 441 being used to extend into cross pin 440 and set push rod 60 in the cross pin 440. The cross pin 440 is fixedly positioned in lever member 420. Upon pivotal motion of lever arm 420, as indicated at 450, using a conventional hand grip as indicated at 455 to apply pressure to extended handle element 456 of lever member 420, push rod 60 will move linearly as indicated at 460 to actuate an end-effector (not shown in FIG. 3a) coupled thereto as hereinabove described. A customary, state-of-the art ratchet type holding mechanism is shown at 425 for locking lever portion 420 relative to handle 410.

Figure 5:
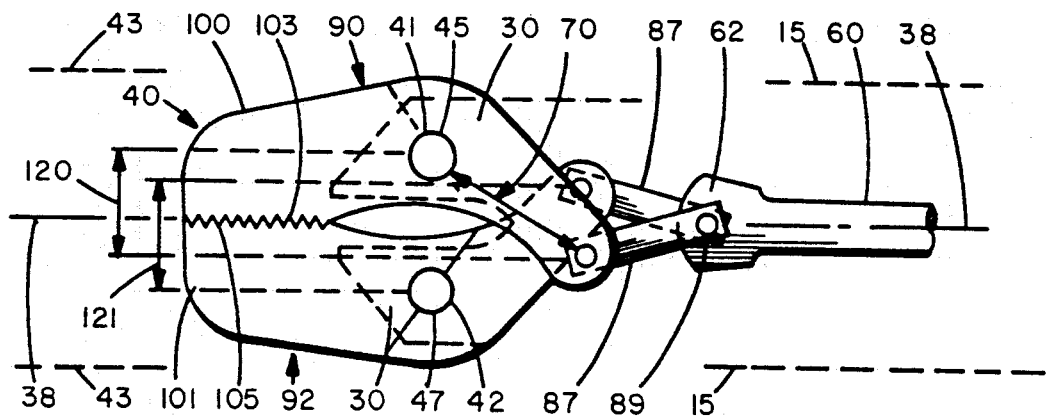
FIG. 5 is a side elevation view of the dual pivot instrument of the present in a closed position.

With reference to FIGS. 5, 5(A), 5(A)-1, 5(B), 5(B)-1, and 5(C), a preferred dual pivot end effector 40, in the form of a grasper, is shown. End effector 40 comprises manipulation members 90, 92 which are separately shown in FIGS. 5(A) and 5(B). For the end effector 40, the manipulation members 90, 92 are essentially identical, with one being inverted 180° with respect to the other when arranged for operation in a laparoscopic instrument as shown in FIG. 5. Manipulation members 90, 92 each have an extended forward edged portion 100, 101, with opposed edges 103, 105 for grasping, cutting and the like. Base members 107, 109, integral with forward edged members are obliquely angled inwardly forward their associated edges 103, 105 as shown at 111, 113. Base member 107, 109 function as lever arms and are provided with through holes 41, 42 for respectively engaging pivot posts 45, 47 of clevis 30 which is shown in "phantom" in FIG. 5.

Figure 7:
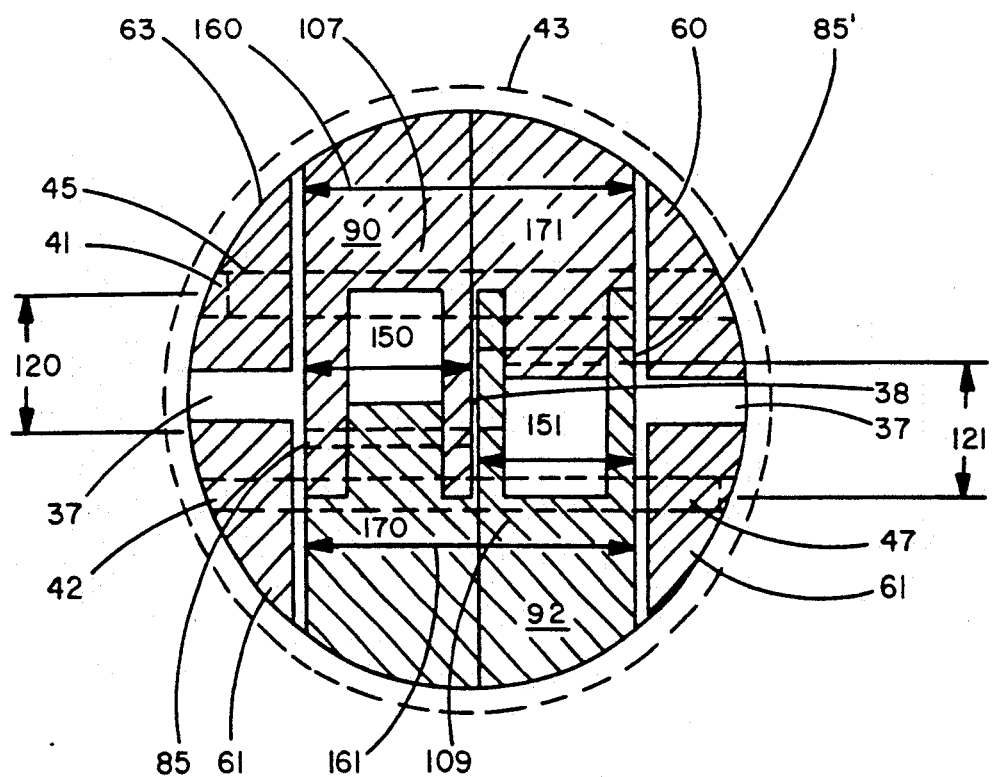
FIG. 7 is a rear sectional elevation view of the device of FIG. 6 along 7—7.

Posts 45, 47 are positioned transverse to longitudinal axis 38 of clevis 30, rod 60 and tube 15 as hereinabove described, and posts 45, 47 are each displaced radially outward and away from longitudinal axis 38 by the distances shown at 120, 121 in FIG. 5 and FIG. 7. The offset distances 120, 121 can be as large or larger than one-half of the diameter 43 of the instrument, and the longer the distances 120, 121, the greater the leverage that can be obtained and the greater the force that can be applied by the manipulation members 90, 92 end effector 40 to large organs and anatomic structures. Displaced posts 45, 47 of the device of FIG. 5 are suitably stainless steel screws which engage holes 41, 42 and are positioned directly opposite to each other in a common transverse plane on opposite sides of the longitudinal axis 38 and are suitably respectively engaged at about the midpoint of clevis quadrant segments 61, 63 shown in FIG. 2d and FIG. 7 which are separated by axial slots 37.

Figure 5C:
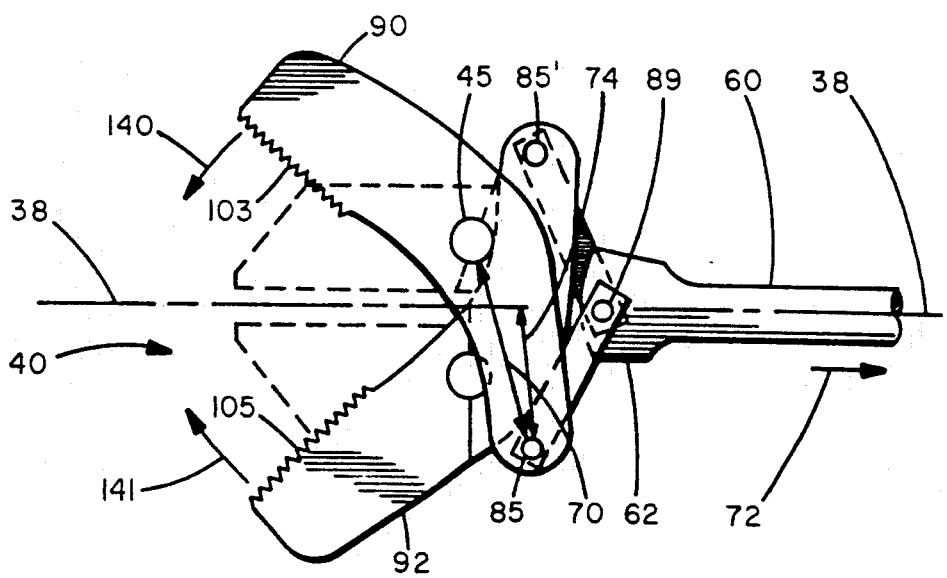
FIG. 5c is a side elevation view of the device of FIG. 5 in an open position.
Figure 6:
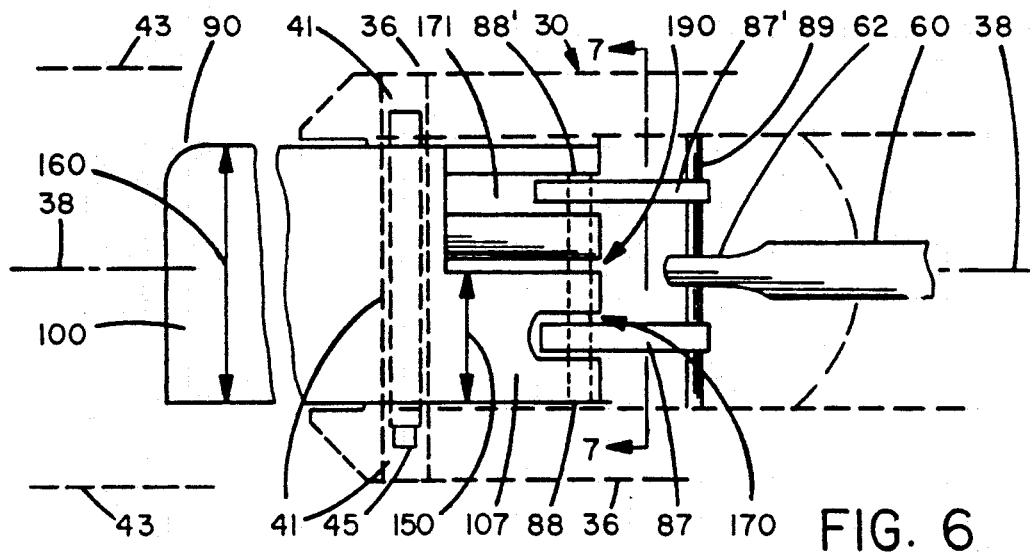
FIG. 6 is a plan view of the device of FIG. 5.

The provision of two separate axially displaced pivot posts 45, 47 for the respective manipulation members 90, 92 in accordance with the present invention establishes a lever arm indicated at 70 in the end effector "open" position of FIG. 5c when push rod 60 is moved in the axial direction indicated at 72. Lever arm 70, for manipulation member 90, is the distance from pivot 45 to the through hole 85 in member 90 which pivotally engages linkage means 87. Linkage means is suitably a thin metal bar e.g. stainless steel, to which flattened portion 62 of push rod 60 is pivotally engaged. Engagement is obtained by transverse pivot rod 89 which passes through hole 93 of metal linkage bar 87.

A comparison between prior art devices such as seen in FIG. 4, and the device of the invention shows that the prior art devices such as device 12 of FIG. 4 have axial offsets 220, 221 which are less than the offsets 120, 121 of the device of FIG. 5 of this invention. Comparison also shows that the lever arm 70 of the device of FIG. 5 is, and can always be greater in length than the lever arm 75 of the prior art axially in-line arrangement of FIG. 4, e.g. by at least the incremental distance shown at 74 in FIG. 5(C). This distance 74 extends from the longitudinal axis 38 to the hole 85 in the base portion of the manipulation member 90.

The offset distance 220 of the prior art device of FIG. 4 is limited to a distance of less than one half of the instrument outline 34. This restriction results in devices with only limited leverage being available. Limited leverage is disadvantageous, especially in manipulating large organs and anatomic parts. On the other hand, the offset distances 120, 121 in the dual pivot device of this invention shown in FIG. 5 can be as much as one half the diameter of the outline and even more, while avoiding protrusion of the linking mechanism members 87, 87' outside of the outline 43 of the instrument.

The above described lever arm relationship of manipulation member 90 also applies to manipulation member 92 as indicated at 70' in FIG. 5a. With the above described dual pivot post configuration, movement of push rod 60 in the direction 72 shown in FIG. 5c causes transverse push rod pivot 89 to move in the same direction, and results in rotation of manipulation members 90, 92 in the directions indicated at 140, 141 in FIG. 5c. Due to the extended lever arms 70, 70' hereinbefore described an increased leverage is developed which results in increased pressure on an organ or vessel positioned adjacently in contact with edges 103, 105. This increased pressure through the utilization of two pivot posts is attainable without any increased protrusion of the mechanism outside of the outline 43 of the laparoscopic instrument. This is due in part to the configuration of the manipulation members 90, 92 whereby the base members 107, 109 thereof have a width 150, 151 which is less than the width 160, 161 of the forward edged portions 100, 101 as shown in FIGS. 5a, 5b, the top plan view of FIG. 6, the rear sectional elevation view of FIG. 7 and the partial perspective view of FIG. 8. In the embodiment shown, the width of the members 107, 109 is slightly less than one-half the width of the forward edged members 100, 101. As also shown in FIGS. 5a, 5b, 6, 7 and 8, the base members 107, 109 have respective slots 170, 171 which receive the end portions 175, 175' of link members 87, 87' which are remote from pivot 89 of the flattened portion 62 of push-rod 60. The end portions 175, 175' of link members 87, 87' are pivotally engaged at holes 85, 85' by pins 88, 88'. Since the widths of base members 107, 109 are less than the full width of the forward edged portions 100, 101, recesses 190, 191 are established laterally adjacent and inward from the base members 107, 109. These recesses 190, 191 respectively receive base members 107, 109 of manipulation members 90, 92 in the course of their pivotal movement during opening and closing of the end effector 40, thus eliminating any interference due to the utilization of dual transverse pivot posts 47, 47' which are aligned in a plane transverse to longitudinal axis 38.

There has been described and illustrated herein a double acting, dual pivot disposable laparoscopic instrument. While particular embodiments of the invention have been described, it is not intended that the invention be limited exactly thereto, as it is intended that the invention be as broad in scope as the art will permit. Thus, while particular end effectors were disclosed, it will be appreciated that other end effectors such as, duck-bill graspers, scissors, duck-bill dissectors, atraumatic graspers, and traumatic (rat-tooth) graspers, among others, could be utilized. Also, while various materials were described as being preferred for various parts, it will be appreciated that other materials could be utilized. By way of example only, and not by way of limitation, while the tube and clevis are preferably made from aluminum alloys, with the clevis being harder than the tube, if desired, the tube could be harder than the clevis. In such a situation, rather than crimping the tube over the clevis, the clevis could be welded or press fit into the tube. Therefore, it will be apparent to those skilled in the art that other changes and modifications may be made to the invention as described in the specification without departing from the spirit and scope of the invention as so claimed.

What is claimed is:

1. A surgical instrument suitable for insertion through a trocar tube for the manipulation of remotely located internal body parts, said instrument comprising:

a) a longitudinally extending push rod having a distal end portion and a proximal end portion remote from said distal end portion, and a longitudinal axis;

b) a longitudinally extending tube surrounding said push rod along most of its length between said distal and proximal end portions thereof;

c) actuating means engaging said push rod at said proximal end thereof for imparting reciprocal axial longitudinal motion to said push rod relative to said tube;

d) a clevis means affixed to said tube member adjacent said distal end of said push rod;

e) first and second post means engaging said clevis means, with said first post means transverse to the longitudinal axis of said push rod, and said second post means transverse to said longitudinal axis, said first and second post means being displaced on opposite sides of said longitudinal axis and being distally spaced from said distal end of said push rod;

f) end effector means having first and second members, said first and second members each having a forwardly extending portion and a rearwardly extending base portion, with each said rearwardly extending base portion having a through-hole located on the other side of said longitudinal axis than the forwardly extending portion of the same member, said first and second members being respectively pivotally mounted on said first and second post means at intermediate locations between the forwardly extending portions and the base portions of the respective members with the forwardly extending portions of the respective members being oppositely disposed;

g) first and second connecting means, each having proximal and distal portions, one of said first and second connecting means engaging with its proximal portion said distal end portion of said push rod and engaging with its distal portion the through-hole in the base portion of one of said first and second manipulation members, and the other of said first and second connecting means engaging with its proximal portion said distal end portion of the push rod and engaging with its distal portion the through-hole in the base portion of the other one of said first and second manipulation members.

2. A surgical instrument according to claim 1, wherein:

said hollow tube, clevis means, and push rod means are formed of aluminum or aluminum base alloys.

3. A surgical instrument according to claim 1, further comprising:

shrink wrap plastic covering substantially all of said hollow tube, and a portion of said clevis means adjacent the first end of the hollow tube.

4. A surgical instrument according to claim 1, wherein:

said end effector is formed of one of investment cast bronze and investment cast stainless steel.

5. A surgical instrument according to claim 1, wherein:

each said base portion is slightly less than one-half the width of said forwardly extending portion.

6. A surgical instrument according to claim 5, wherein:

each said base portion further comprises a slot into which the terminal portion of a respective said connecting means fits.

7. In a surgical instrument suitable for insertion through a trocar tube and having an outer tube having proximal and distal ends and a longitudinal axis, a push rod having proximal and distal ends and extending at least partially through said outer tube, a clevis means engaging said distal end of said outer tube, first and second manipulation members each having a through-hole, and first and second connecting means for coupling said distal end of said push rod to said first and second manipulation members, an improvement comprising:

first and second pivot posts engaging said clevis means, said first pivot post extending through said through-hole of said first manipulation member and said second pivot post extending through said through-hole of said second manipulation member, said first and second pivot posts extending transverse to said longitudinal axis of said outer tube and respectively positioned on opposite sides of said longitudinal axis and displaced therefrom, wherein said first connecting means engages said first manipulation member at a location along said first manipulation member on the opposite side of said longitudinal axis to where said first pivot post engages said first manipulation member, and said second connecting means engages said second manipulation member at a location along said second manipulation member on the opposite side of said longitudinal axis to where said second pivot post engages said second manipulation member.

8. In a surgical instrument according to claim 7, wherein:
said first and second manipulation members have respective forward extending opposed portions and respective base portions integral with said forward extending portions, said base portions being at an oblique angle with said forward extending portions.

9. In a surgical instrument according to claim 8, wherein:
each of said base portions have a width which is less than that of the forward portion with which it is integral.

10. In a surgical instrument according to claim 9, wherein:
each said base portion has a recess which receives the other base portion.

11. In a surgical instrument according to claim 10, wherein:
each said base portion extends toward said longitudinal axis at an oblique angle with respect to said forward portion with which it is integral.

12. In a surgical instrument according to claim 11, wherein:
said base member of said first manipulation means has a slot which receives said first connecting means, and said base member of said second manipulation means has a slot which receives said second connecting means.

13. In a surgical instrument according to claim 12, wherein:
said first and second manipulation members are substantially identical and are arranged with their respective recesses oppositely adjacent.

14. In a surgical instrument according to claim 13, wherein:
the width of each base member is less than one half the width of a forward extending portion.

15. A surgical instrument insertable through a trocar tube of fixed diameter for the manipulation of remotely located internal body parts, said instrument comprising:

a) a longitudinally extending push rod having a first end portion and a second end portion remote from said first end portion, said push rod having a longitudinal axis, and said first end portion having a through-hole transverse and substantially on the longitudinally axis of said push rod;

b) a longitudinally extending tube surrounding said push rod along most of its length between said first and second end portions thereof;

c) actuating means engaging said push rod at said second end thereof for imparting reciprocal axial longitudinal motion to said push rod relative to said tube;

d) first and second post means coupled to said longitudinally extending tube and fixed relative to said longitudinally extending tube, with said first and second post means transverse to the longitudinal axis of said push rod, and displaced on opposite sides of said longitudinal axis, said first and second post means being distally spaced from said first end of said push rod;

e) end effector means having first and second manipulation members, said first and second manipulation members each having a forwardly extending portion and a rearwardly extending base portion, with each said rearwardly extending base portion having a through-hole located on the other side of said longitudinal axis than the forwardly extending portion of the same manipulation member, said first and second manipulation members being respectively pivotally mounted on said first and second post means at intermediate locations between the forwardly extending portions and the base portions of the respective manipulation members with the forwardly extending portions of the respective manipulation members being oppositely disposed;

f) first and second connecting means, each having proximal and distal portions, one of said first and second connecting means coupled at its proximal protion to said push rod at said through-hole of said push rod and coupled at its distal portion the through-hole in the base portion of one of said first and second manipulation members, and the other of said first and second connecting means coupled at its proximal portion to said push rod at said through-hole said push rod and coupled at its distal portion the through-hole in the base portion of the other one of said first and second manipulation members.

16. A surgical instrument according to claim 15, wherein:
the sum of the distances perpendicular to said longitudinal axis traversed by said first and second connecting means is at least as great as the inner diameter of said trocar tube.

17. A surgical instrument according to claim 15, further comprising:
g) a clevis means for coupling said first and second post means to said longtiduinally extending tube member, said clevis means being affixed to said tube member adjacent said first end of said push rod, and receiving said first and second post means.

18. A surgical instrument according to claim 16, wherein:
each said base portion of said manipulation members is at an oblique angle relative to a said forwardly extending portion of a respective manipulation member.

19. A surgical instrument according to claim 18, wherein:

each of said base portions has a width which is less than about one half the width of said forwardly extending portions, and each said base portion has a recess which receives said other base portion, said first and second manipulation members being substantially identical and arranged with their respective recesses oppositely adjacent.

20. A surgical instrument according to claim 19, wherein:

said base member of said first manipulation member has a slot which receives said first connecting means, and said base member of said second manipulation means has a slot which receives said second connecting means.

* * * * *